United States Patent [19]
Osugi et al.

[11] Patent Number: 4,547,482
[45] Date of Patent: Oct. 15, 1985

[54] CATALYST COMPOSITION SUITED FOR SYNTHESIS OF METHANOL

[75] Inventors: Minoru Osugi; Tadasi Nakamura; Shuji Ebata, all of Niigata, Japan

[73] Assignee: Mitsubishi Gas Chemical Company, Inc., Tokyo, Japan

[21] Appl. No.: 515,933

[22] Filed: Jul. 20, 1983

[30] Foreign Application Priority Data

Jul. 21, 1982 [JP] Japan .................. 57-127296

[51] Int. Cl.$^4$ .................. B01J 23/80; B01J 27/18
[52] U.S. Cl. .................. 502/208; 502/183; 502/184; 502/343; 502/345; 518/713
[58] Field of Search ............... 502/182, 183, 184, 208, 502/344, 345, 179, 343; 518/713

[56] References Cited
U.S. PATENT DOCUMENTS

| | | | |
|---|---|---|---|
| 3,248,432 | 4/1966 | Riley et al. | 502/208 |
| 3,928,483 | 12/1975 | Chang et al. | 585/407 |
| 3,971,735 | 7/1976 | Asano et al. | 502/202 |
| 4,181,630 | 1/1980 | Baglin et al. | 502/345 |
| 4,279,781 | 7/1981 | Dienes et al. | 502/343 |
| 4,305,842 | 12/1981 | Asakawa et al. | 502/202 |
| 4,423,155 | 12/1983 | Bell et al. | 502/208 |
| 4,436,835 | 3/1984 | Horie et al. | 502/208 |

Primary Examiner—D. E. Gantz
Assistant Examiner—Anthony McFarlane
Attorney, Agent, or Firm—Wenderoth, Lind & Ponack

[57] ABSTRACT

A catalyst composition comprising copper oxide, zinc oxide and an oxyacid of phosphorus or its salt; and a method for producing methanol by reacting carbon monoxide and/or carbon dioxide with hydrogen in the vapor phase in the presence of a catalyst, wherein the catalyst is the aforesaid catalyst composition which has been activated by reduction with a hydrogen-containing gas.

11 Claims, No Drawings

CATALYST COMPOSITION SUITED FOR SYNTHESIS OF METHANOL

This invention relates to a novel catalyst composition. More specifically, this invention relates to a catalyst composition having excellent catalytic activity and high mechanical strength which is suitable for use in synthesizing methanol from carbon monoxide and/or carbon dioxide and hydrogen by a vapor-phase method.

Heretofore, catalysts of the zinc-chromium type or the copper-zinc-chromium type have been used widely for the synthesis of methanol from carbon monoxide and/or carbon dioxide and hydrogen by a vapor-phase method. In recent years, there have been proposed catalysts composed of oxides of copper, zinc and aluminum (see British Pat. Nos. 1,159,035 and 1,286,970) and catalysts composed of oxides of copper, zinc, aluminum and boron (see U.S. Pat. No. 3,971,735 and British Pat. No. 2,064,352A). These catalysts have much improved activity over conventional catalysts, and enable methanol to by synthesized at lower temperatures and pressures. However, they have not proved to be entirely satisfactory for commercial practice in regard to catalytic activity and mechanical strength. It has therefore been desired to develop a catalyst having excellent activity and mechanical strength.

The present inventors have made extensive investigations in order to develop a catalyst having improved catalytic activity and high mechanical strength suitable for synthesis of methanol, which catalyst can be prepared by a simplified manufacturing process. These investigations have led to the discovery that a catalyst comprising copper, zinc, and an oxyacid of phosphorus or its salt has superior performance in the synthesis of methanol from carbon monoxide and/or carbon dioxide and hydrogen by a vapor-phase method.

According to this invention, there is provided a catalyst composition comprising copper oxide, zinc oxide and an oxyacid of phosphorus or its salt.

The catalyst of this invention consists essentially of an intimate mixture of three essential components, copper oxide, zinc oxide and an oxyacid of phosphorus or its salt, and as required a lubricant.

The "oxyacid of phosphorus or its salt" constituting one component of the catalyst includes, for example, orthophosphoric acid, pyrophosphoric acid, polyphosphoric acid, metaphosphoric acid, phosphorous acid, hypophosphorous acid and metal salts of these acids. There is no particular restriction on the metals forming the metal salts, but inclusion of oxygen-family elements (excepting oxygen) such as sulfur, halogen family elements, and alkali metals such as sodium and potassium should be avoided.

Specific examples of such metal salts are orthophosphates such as copper phosphate, silver phosphate, magnesium phosphate, magnesium hydrogen phosphate, magnesium dihydrogen phosphate, calcium phosphate, calcium hydrogen phosphate, calcium dihydrogen phosphate, strontium phosphate, barium hydrogen phosphate, zinc phosphate, cadmium phosphate, aluminum phosphate, tin phosphate, lead phosphate, lead hydrogen phosphate, titanyl phosphate, zirconyl phosphate, bismuth phosphate, chromium phosphate, manganese phosphate, manganese hydrogen phosphate, ferrous phosphate, ferric phosphate, cobalt phosphate and nickel phosphate; pyrophosphates such as copper pyrophosphate, magnesium pyrophosphate, calcium pyrophosphate, zinc pyrophosphate and manganese pyrophosphate; polyphosphates such as calcium tripolyphosphate and magnesium tripolyphosphate; metaphosphates such as magnesium metaphosphate, calcium metaphosphate, barium metaphosphate and aluminum metaphosphate; phosphites such as magnesium phosphite, calcium phosphite, germanium phosphite and lead phosphite (dibasic); and hypophosphites such as magnesium hypophosphite, calcium hypophosphite, barium hypophosphite and manganese hypophosphite. Among these oxyacids of phosphorus and their salts, magnesium phosphate, calcium hydrogen phosphate, calcium phosphite, calcium phosphate, zirconyl phosphate, magnesium pyrophosphate, calcium pyrophosphate, magnesium tripolyphosphate and calcium metaphosphate are especially preferred for use in this invention.

The proportions of copper oxide, zinc oxide and an oxyacid of phosphorus or its salt present in the catalyst composition of this invention are not critical, and can be varied depending upon such factors as the type of the oxyacid of phosphorus or its salt and conditions under which the catalyst composition is used. Generally, copper oxide, zinc oxide, and the oxyacid of phosphorous or its salt are present in the following atomic percentages based on the total amount of Cu, Zn and P atoms in the above three active catalyst ingredients.

| Catalyst ingredient | General | Preferred | Optimum |
|---|---|---|---|
| Copper oxide (as Cu) | 17–90 atm. % | 25–85 atm. % | 33–73 atm. % |
| Zinc oxide (as Zn) | 9–83 atm. % | 14–75 atm. % | 24–66 atm. % |
| Oxyacid of phosphorus or its salt (as P) | 0.02–15 atm. % | 0.1–10 atm. % | 0.5–5 atm. % |

Advantageously, in the catalyst composition of this invention, copper oxide and zinc oxide are present in such proportions that the Cu/Zn atomic ratio is generally from 0.2 to 10, preferably from 0.3 to 5, more preferably from 0.5 to 3. The oxyacid of phosphorus or its salt is suitable present in such a proportion that the P/Zn atomic ratio is generally from 0.002 to 0.2, preferably from 0.005 to 0.15, more preferably from 0.01 to 0.1.

In addition to the three catalyst ingredients described above, i.e. copper oxide, zinc oxide and the oxyacid of phosphorus or its salt, the catalyst composition of this invention may further contain a lubricant which is catalytically inert. Graphite known with regard to catalyst compositions of this type is used as the lubricant. The amount of the lubricant may be generally at most 10% by weight, preferably at most 5% by weight, more preferably 2 to 4% by weight, based on the total weight of the catalyst composition.

The catalyst composition of this invention can be produced in the same way as in the prior art described above. Basically, it can be produced, for example, by uniformly mixing an oxyacid of phosphorus or its salt to a mixture of a water-insoluble copper compound and a water-insoluble zinc compound convertible to copper oxide and zinc oxide respectively under the calcination conditions to be described hereinbelow, and subjecting the resulting mixture to calcination treatment. A method for preparing the catalyst composition of this invention is described below in greater detail.

The mixture of the water-insoluble copper compound and zinc compound convertible to copper oxide and zinc oxide under the calcination conditions to be described hereinbelow can be produced, for example, by the following methods.

(a) A method which comprises adding an alkaline precipitating agent to an aqueous solution containing both a water-soluble copper salt and a water-soluble zinc salt to co-precipitate a water-insoluble copper compound and a water-insoluble zinc compound.

(b) A method which comprises precipitating a water-insoluble copper compound and a water-insoluble zinc compound separately from an aqueous solution of a water-soluble copper salt and an aqueous solution of a water-soluble zinc salt by using an alkaline precipitating agent, and mixing the precipitates.

(c) A method which comprises adding zinc oxide or zinc hydroxide to a water-insoluble copper compound precipitated from an aqueous solution of a water-soluble copper salt by using an alkaline precipitating agent, thereby to form an aqueous slurry, and blowing carbon dioxide gas into the aqueous slurry to convert zinc oxide or zinc hydroxide to basic zinc carbonate.

Water-soluble copper compounds used as starring materials in these methods include water-soluble copper salts usually employed for the preparation of the aforesaid conventional catalysts. Specific examples are cupric nitrate, cupric acetate and cupric oxalate. Those which do not contain elements acting as catalyst poisons such as halogen or sulfur are preferred. Cupric nitrate is especially preferred.

Water-soluble zinc compounds may be any water-soluble zinc salts which are usually employed for the preparation of the aforesaid conventional catalysts. Specific examples include zinc nitrate and zinc acetate. Of these salts, preferred are those not containing elements that become catalyst poisons such as halogen or sulfur. Zinc nitrate is particularly preferred.

The concentration of a water-soluble salt of copper and/or a water-soluble salt of zinc in an aqueous solution thereof from which a water-insoluble copper compound and/or a water-insoluble zinc compound is to be precipitated is not critical, and can be varied widely depending upon the types of such salts, etc. Generally, it is 0.1 mole/liter to the limit of dissolution of the salt, preferably 0.3 to 1 mole/liter.

Examples of the alkaline precipitating agent used for precipitating a copper component and a zinc component as insoluble solids from an aqueous solution of such a water-soluble copper salt and/or a water-soluble zinc salt include ammonia, and alkali carbonates, bicarbonates and hydroxides, such as sodium carbonate, sodium bicarbonate, ammonium carbonate, ammonium bicarbonate, sodium hydroxide and potassium hydroxide. These precipitating agents may be used as such or as aqueous solutions. In any case, it is advantageous to use the alkaline precipitating agent in a proportion of at least 0.8 equivalent, preferably 1.0 to 2.0 equivalents, more preferably 1.0 to 1.3 equivalents, per equivalent of the copper salt and zinc salt.

Coprecipitation of the water-insoluble copper compound and the water-insoluble zinc compound from the aqueous solution of the water-soluble copper salt and the water-soluble zinc salt [method (a) described above] and separate precipitations of these water-insoluble compounds [method (b) described above] can be effected by known methods. For example, coprecipitation in accordance with method (a) can be carried out in accordance with the method described in U.S. Pat. No. 3,971,735. Separate precipitation in accordance with method (b) may be carried out by the method described in U.S. Pat. No. 4,305,842. The disclosures of these U.S. Patents are incorporated herein in lieu of a specific description of these methods (a) and (b).

Conversion of zinc oxide or zinc hydroxide in the aqueous slurry containing zinc oxide or zinc hydroxide into basic zinc carbonate by method (c) is also known, and can be carried out, for example, by the method described in the published specification of U.K. patent application No. 2064352A. The disclosure of this U.K. specification is also incorporated herein in lieu of a specific disclosure of the method (c).

The oxyacid of phosphorus or its salt is then added to the mixture of a water-insoluble copper compound such as basic copper carbonate $[Cu(OH)_2CuCO_3]$ and a water-insoluble zinc compound such as basic zinc carbonate $[2ZnCO_3 \cdot 3Zn(OH)_2 \cdot H_2O]$, which is prepared as described above.

When the oxyacid of phosphorus or its salt to be added is substantially insoluble in water, it may be added in the form of a fine powder having an average particle diameter of, for example, not more than 100 microns, preferably not more than 50 microns, to an aqueous slurry of the water-insoluble copper compound and the water-insoluble zinc compound (to be referred to as an "aqueous Cu—Zn slurry") directly. Advantageously, however, the fine powder is dispersed in water in advance to prepare an aqueous slurry which is then added to, and uniformly mixed with, the aforesaid aqueous Cu—Zn slurry.

When the oxyacid of phosphorus or its salt to be added is water-soluble, the oxyacid of phosphorus or its salt is added, either as a fine powder or as a solution having a concentration of generally 1 to 10% by weight, preferably 5 to 10% by weight, to a solid mixture of the water-insoluble copper compound and the water-insoluble zinc compound, followed by thorough mixing.

The so prepared mixture of the water-insoluble copper compound, the water-insoluble zinc compound and the oxyacid of phosphorus or its salt is calcined after it is optionally subjected to such treatments as kneading or drying. The calcination may be performed by a method known per se. For example, the mixture is calcined by heating it at a temperature of at least 300° C., preferably 330° to 400° C., usually for about 0.5 to 3 hours in an atmosphere of air, a combustible gas, etc. in a calcination furnace such as an electrical furnace or a gas calcination furnace. As a result of this calcination, the copper component and the zinc component are each converted to an oxide form.

The catalyst so obtained can be pulverized and, after optionally adding the aforesaid lubricant, molded by a tableting machine. Usually, one molding cycle is enough to afford a molded catalyst composition having sufficient strength as a commercial catalyst. As required, however, it may be molded by pulverizing it, pre-molding the pulverized product by a molding machine, further pulverizing the pre-molded product, and then compression-molding it into tablets.

Depending upon the conditions for catalyst preparation, the resulting catalyst composition having the aforesaid components in the specified proportions may further contain a small amount of a metal atom. For example, an alkali metal atom may be incorporated into it in an amount of 100 to 400 ppm.

The catalyst composition of this invention, after it is subjected to an activation treatment such as reduction with hydrogen as is usually practiced, can be used as a catalyst for various reactions, for example a reaction of synthesizing methanol from a gaseous mixture of carbon monoxide and/or carbon dioxide and hydrogen, a carbon monoxide conversion reaction, a hydrogenation reaction, and a methanol decomposition reaction.

The activation treatment of the catalyst composition of the invention may be carried out in a customary manner, for example, by reducing it with a hydrogen-containing gas. For example, it is carried out in a reducing atmosphere such as a starting gas for synthesis of methanol by raising the temperature for the catalyst composition gradually from about 140° C. to avoid abrupt generation of heat, and finally maintaining the catalyst composition at 240° C. for 3 hours.

The activated catalyst composition is particularly suitable for catalyzing synthesis of methanol from a gaseous mixture of carbon monoxide and/or carbon dioxide and hydrogen. Synthesis of methanol with the catalyst composition of this invention can be carried out by a method known per se, for example, by the method described in U.S. Pat. No. 3,971,735. For example, the synthesis reaction can be performed by feeding the aforesaid gaseous mixture into a reaction zone at a pressure of 20 to 300 atmospheres, preferably 30 to 150 atmospheres, a temperature of 150° to 300° C., preferably 200° to 280° C., and a space velocity of 2,000 to 50,000 $hr^{-1}$.

The catalyst composition provided by the process of this invention has various excellent advantages over conventional catalysts of the same type, and is very suitable for synthesis of methanol. Among these advantages are:

1. Its activity in methanol synthesis is greatly increased.
2. It has excellent mechanical strengths such as resistance to powderization.
3. The method of preparing the catalyst is simple, and it can be prepared at low cost.

The following examples illustrate the present invention in greater detail.

EXAMPLE 1

Copper nitrate trihydrate (390 g) and 560 g of zinc nitrate hexahydrate were dissolved in 5 liters of deionized water, and the solution was maintained at 80° C. A solution of 360 g of sodium carbonate in 4.3 liters of deionized water, maintained at 80° C., was added to the above solution to co-precipitate the copper component and the zinc component and to form a slurry. The slurry was stirred for 30 minutes at this temperature, and aged. Then, a slurry of each of the various oxyacids of phosphorus or salts thereof indicated in Table 1 (Example 1-A to 1-M) was added. The concentration of the oxyacid of phosphorus or its salt in the slurry was adjusted to 10% by weight in all runs.

After the addition of the oxyacid of phosphorus or its salt, the mixture was stirred for 20 minutes, and filtered by a filter press. The resulting filter cake was washed with water, dried at 100° C. for 17 hours, and then calcined in a calcination furnace at 370° C. for 2.5 hours. After the calcination, the resulting catalyst was pulverized to a size of 14 mesh or smaller, and mixed with 3% by weight, based on the pulverized catalyst, of graphite. The mixture was molded into a small solid cylindrical form. In this manner, catalysts 1A to 1M indicated in Table 1 were prepared.

EXAMPLE 2

A Cu—Zn slurry obtained in the same way as in Example 1 was stirred at 80° C. for 30 minutes, aged, and filtered by a filter press. The filter cake was washed with water, and mixed with an aqueous solution of each of various phosphates indicated in Table 1 (Example 2-A to 2-C). They were kneaded for 30 minutes by a kneader. In all runs, the concentration of the phosphate in the aqueous solution was adjusted to 5% by weight.

The slurry after kneading was dried at 100° C. for 17 hours, and thereafter worked up in the same way as in Example 1. In this manner, catalysts 2A to 2C were prepared.

EXAMPLE 3

Copper nitrate trihydrate (585 g) was dissolved in 4.5 liters of deionized water, and the solution was maintained at about 30° C. A solution of 402 g of ammonium bicarbonate in 3.4 liters of deionized water, maintained at about 30° C., was added to the above aqueous copper nitrate solution with stirring to prepare a copper slurry.

Separately, 148.2 g of zinc oxide was added to 1.2 liters of deionized water, and they were stirred for 30 minutes to prepare a zinc oxide slurry. With stirring, the zinc oxide slurry was added to the copper slurry, and carbon dioxide gas was blown into the mixture. The temperature of the mixture at this time was maintained at about 30° C., and the carbon dioxide gas was blown at a rate of 9.3 Nl/hr for 2 hours.

While the carbon dioxide gas was continued to be blown into the solution, the temperature of the solution was raised to 80° C. The solution was further stirred at this temperature for 30 minutes to age it. A slurry of each of the phosphates shown in Table 1 (Examples 3-A to 3-N) (concentration 10% by weight) was added to the aged solution. The mixture was worked up in the same way as in Example 1. In this manner, catalysts 3A to 3N were prepared.

EXAMPLE 4

A copper-zinc oxide slurry prepared as in Exmaple 3 was stirred at 80° C. for 30 minutes while carbon dioxide was blown into it at a rate of 9.3 Nl/hr. The aged mixture was filtered by a filter press. The filtration cake was washed with water, and mixed with an aqueous solution of each of the aqueous solutions of phosphates shown in Table 1 (Example 4-A or 4-B) (concentration 5% by weight). They were kneaded for 30 minutes by a kneader. The mixture was worked up in the same way as in Example 2. In this manner, catalysts 4A and 4B were prepared.

COMPARATIVE EXAMPLE 1

A catalyst X was prepared in the same way as in Example 2 except that 120 g of alumina sol (containing 10% by weight of alumina) was added instead of the aqueous solution of phosphate.

COMPARATIVE EXAMPLE 2

A catalyst Y was prepared in the same way as in Example 4 except that 180 g of alumina sol (containing 10% by weight of alumina) was added instead of the aqueous solution of phosphate.

REFERENTIAL EXAMPLE 1

Activity Test

Each of the catalysts produced in Examples 1 to 4 and Comparative Examples 1 and 2 was pulverized to a size of 20 to 40 mesh, and maintained at 140° C. in a stream of nitrogen gas. To avoid abrupt heat generation, the temperature was elevated while gradually adding synthesis gas, and finally, the catalyst was maintained at 240° C. for 3 hours to reduce it.

Then, methanol was synthesized from a methanol decomposition gas composed of 70% of $H_2$, 23% of CO, 3% of $CO_2$, 3.5% of $CH_4$ and 0.5% of $N_2$ at a pressure of 70 atmospheres, a space velocity of $2 \times 10^4$ $hr^{-1}$ and a temperature of 260° C.

To determine the life of the catalyst within a short period of time, the temperature of the catalyst was raised to 360° C., and methanol synthesis was carried out for 2 hours. Its temperature was then again lowered to 260° C., and its catalytic activity was measured. Furthermore, the catalyst was further used in methanol synthesis at 360° C. for 8 hours (10 hours in total) and then the temperature of the catalyst was lowered to 260° C. Its activity at this time was also measured. The catalyst activities are shown in terms of the concentration of methanol in the exit gas in Table 1.

These results demonstrate that the copper-zinc-phosphate type catalysts of this invention have much better activity in methanol synthesis than the copper-zinc-alumina type catalysts of Comparative Examples 1 and 2.

REFERENTIAL EXAMPLE 2

Strength Test

The compression strength in the longitudinal direction (in the direction of the central axis) of typical examples of small cylindrical catalysts obtained in Examples 1 to 4 and Comparative Examples 1 and 2 before and after reduction were measured by using a small-sized material tester (Model PSP-300, manufactured by Fujii Seiki Co., Ltd.).

The grams each of the aforesaid catalysts before and after reduction was put in a cylindrical drum having a diameter of 100 mm and equipped with a wire gauze (6 mesh according to JIS) applied to its circumferential surface, and the drum was rolled for 20 minutes at 160 rpm. The percent pulverization of each catalyst was calculated from the following equation.

$$\text{Percent powderization (\%)} = \frac{[\text{Amount of sample collected (g)}] - [\text{Amount of sample remaining in the drum (g)}]}{\text{Amount of sample collected (g)}} \times 100$$

The results are shown in Table 2.

These results demonstrate that the copper-zinc-phosphate type catalysts of this invention have a much lower percent powderization than the copper-zinc-alumina type catalysts of Comparative Examples when they have substantially the same strength.

TABLE 1

| | Oxyacid of phosphorus or its salt | Cu:Zn:P (atomic ratio) | Initial | High temperature treatment 2 hours | High temperature treatment 10 hours |
|---|---|---|---|---|---|
| Example 1-A | Lithium phosphate | 1.333:1.000:0.013 | 16.6 | 15.3 | 15.1 |
| B | Copper phosphate | 1.333:1.000:0.025 | 16.7 | 15.6 | 15.4 |
| C | Magnesium phosphate | 1.333:1.000:0.025 | 18.7 | 17.4 | 17.0 |
| D | Calcium hydrogen phosphate | 1.333:1.000:0.041 | 19.1 | 18.5 | 17.7 |
| E | Zinc phosphate | 1.333:1.000:0.025 | 18.5 | 16.0 | 15.6 |
| F | Manganese phosphate | 1.333:1.000:0.012 | 18.7 | 15.9 | 15.7 |
| G | Ferrous phosphate | 1.333:1.000:0.025 | 16.2 | 15.8 | 15.5 |
| H | Manganese pyrophosphate | 1.333:1.000:0.036 | 17.3 | 16.0 | 15.9 |
| I | Calcium tripolyphosphate | 1.333:1.000:0.050 | 17.8 | 17.5 | 16.9 |
| J | Barium metaphosphate | 1.333:1.000:0.041 | 17.7 | 17.2 | 16.6 |
| K | Calcium phosphite | 1.333:1.000:0.074 | 18.1 | 17.4 | 17.2 |
| L | Orthophosphate | 1.333:1.000:0.015 | 16.5 | 15.2 | 14.9 |
| M | " | 1.333:1.000:0.025 | 15.3 | 14.0 | 13.9 |
| Example 2-A | Magnesium dihydrogen phosphite | 1.333:1.000:0.040 | 16.6 | 15.6 | 15.3 |
| B | Calcium dihydrogen phosphite | 1.333:1.000:0.066 | 16.8 | 16.1 | 15.7 |
| C | Lithium metaphosphate | 1.333:1.000:0.067 | 16.2 | 15.4 | 15.2 |
| Example 3-A | Lithium phosphate | 1.329:1.000:0.012 | 17.3 | 15.9 | 15.8 |
| B | Calcium phosphate | 1.329:1.000:0.018 | 19.4 | 18.5 | 17.9 |
| C | Barium hydrogen phosphate | 1.329:1.000:0.039 | 17.9 | 17.0 | 16.7 |
| D | Zinc phosphate | 1.329:1.000:0.041 | 17.2 | 16.3 | 15.8 |
| E | Lead phosphate | 1.329:1.000:0.020 | 16.8 | 15.6 | 15.5 |
| F | Zirconyl phosphate | 1.329:1.000:0.062 | 18.4 | 17.9 | 17.2 |
| G | Chromium phosphate | 1.329:1.000:0.070 | 16.5 | 16.0 | 15.4 |
| H | Ferric phosphate | 1.329:1.000:0.020 | 16.3 | 15.3 | 15.2 |
| I | Magnesium pyrophosphate | 1.329:1.000:0.033 | 18.9 | 17.5 | 17.1 |
| J | Calcium pyrophosphate | 1.329:1.000:0.033 | 19.0 | 17.4 | 17.3 |
| K | Magnesium tripolyphosphate | 1.329:1.000:0.050 | 18.6 | 17.8 | 17.0 |
| L | Magnesium metaphosphate | 1.329:1.000:0.040 | 18.5 | 17.2 | 16.9 |
| M | Calcium metaphosphate | 1.329:1.000:0.040 | 18.7 | 17.7 | 17.3 |
| N | Magnesium phosphite | 1.329:1.000:0.073 | 18.0 | 16.8 | 16.7 |
| Example 4-A | Calcium hypophosphite | 1.329:1.000:0.068 | 16.7 | 15.6 | 15.4 |
| B | Manganese hypophosphite | 1.329:1.000:0.068 | 16.1 | 15.2 | 15.0 |
| Comparative Example 1-X | | 1.329:1.000:0.097 | 12.6 | 11.8 | 11.2 |
| 2-Y | | 1.329:1.00:0.097 | 14.1 | 113.3 | 12.6 |

TABLE 2

| | Compression strength (kg/cm$^2$) | | Percent powderization (%) | |
| --- | --- | --- | --- | --- |
| | Before reduction | After reduction | Before reduction | After reduction |
| Example | | | | |
| 1-A | 253 | 240 | 1.7 | 2.6 |
| B | 260 | 252 | 1.5 | 2.5 |
| C | 254 | 251 | 1.5 | 2.4 |
| 2-A | 259 | 248 | 1.3 | 1.9 |
| B | 273 | 259 | 1.5 | 1.9 |
| C | 247 | 245 | 1.0 | 1.7 |
| 3-A | 265 | 260 | 1.4 | 1.9 |
| B | 248 | 241 | 1.3 | 2.0 |
| C | 286 | 267 | 2.2 | 3.3 |
| 4-A | 263 | 260 | 1.4 | 2.5 |
| B | 256 | 252 | 1.5 | 2.7 |
| Comparative Example | | | | |
| 1-X | 255 | 251 | 5.9 | 8.1 |
| 2-Y | 271 | 272 | 7.0 | 88.2 |

What we claim is:

1. A catalyst composition for the vapor phase production of methanol from carbon monoxide and/or carbon dioxide and hydrogen consisting essentially of copper oxide, zinc oxide and an oxyacid of phosphorus or its salt.

2. The catalyst composition of claim 1 wherein the proportions of copper oxide, zinc oxide and the oxyacid of phosphorus or its salt are 17 to 90 atomic % of Cu, 9 to 83 atomic % of Zn and 0.02 to 15 atomic % of P based on the total amount of Cu, Zn and P atoms contained in said components.

3. The catalyst composition of claim 2 wherein the proportions of copper oxide, zinc oxide and the oxyacid of phosphorus or is salt are 25 to 85 atomic % of Cu, 14 to 75 atomic % of Zn and 0.1 to 10 atomic % of P based on the total amount of Cu, Zn and P atoms contained in these components.

4. The catalyst composition of claim 1 wherein the proportions of copper oxide and zinc oxide are such that the Cu/Zn atomic ratio is from 0.2 to 10.

5. The catalyst composition of claim 4 wherein the Cu/Zn atomic ratio is from 0.3 to 5.

6. The catalyst composition of claim 1 wherein the proportion of the oxyacid of phosphorus or its salt with respect to zinc oxide is such that the P/Zn atomic ratio is from 0.002 to 0.2.

7. The catalyst composition of claim 6 wherein the P/Zn atomic ratio is from 0.005 to 0.15.

8. The catalyst composition of claim 1 wherein the oxyacid of phosphorus or its salt is selected from the group consisting of orthophosphoric acid, pyrophosphoric acid, polyphosphoric acid, metaphosphoric acid, phosphorous acid, hypophosphorous acid, and metal salts of these acids.

9. The catalyst composition of claim 8 wherein the oxyacid of phosphorus or its salt is selected from the group consisting of magnesium phosphate, calcium hydrogen phosphate, calcium phosphate, calcium phosphite, zirconyl phosphate, magnesium pyrophosphate, calcium pyrophosphate, magnesium tripolyphosphate and calcium metaphosphate.

10. The catalyst composition of claim 1 which further comprises graphite as a lubricant.

11. The catalyst composition of claim 10 wherein the amount of graphite is at most 10% by weight based on the weight of the catalyst composition.

* * * * *